US012667670B2

(12) United States Patent (10) Patent No.: US 12,667,670 B2

Earwalker et al. (45) Date of Patent: Jun. 30, 2026

(54) DOSE COUNTING SYSTEM

(71) Applicant: Sanofi, Paris (FR)

(72) Inventors: Tom Alexander Earwalker, Warwick (GB); Adam Moyo Harvey-Cook, Billericay (GB); Matthew Francis Hobson, Warwick (GB); Oliver Charles Gazeley, Basel (CH)

(73) Assignee: Sanofi, Paris (FR)

( * ) Notice: Subject to any disclaimer, the term of this patent is extended or adjusted under 35 U.S.C. 154(b) by 422 days.

(21) Appl. No.: 18/275,919

(22) PCT Filed: Feb. 7, 2022

(86) PCT No.: PCT/EP2022/052801

§ 371 (c)(1),
(2) Date: Aug. 4, 2023

(87) PCT Pub. No.: WO2022/171548

PCT Pub. Date: Aug. 18, 2022

(65) Prior Publication Data

US 2024/0100259 A1 Mar. 28, 2024

(30) Foreign Application Priority Data

Feb. 9, 2021 (EP) ...................................... 21315018

(51) Int. Cl.
A61M 5/315 (2006.01)
G16H 20/17 (2018.01)

(52) U.S. Cl.
CPC .......... A61M 5/3155 (2013.01); G16H 20/17 (2018.01); *A61M 2205/3306* (2013.01); *A61M 2205/50* (2013.01); *A61M 2205/8212* (2013.01)

(58) Field of Classification Search
CPC ...... A61M 2205/3306; A61M 2205/50; A61M 2205/8212; A61M 5/3155
See application file for complete search history.

(56) References Cited

U.S. PATENT DOCUMENTS 9,623,188 B2 4/2017 Nielsen et al.
2014/0194825 A1 7/2014 Nielsen et al.
(Continued)

FOREIGN PATENT DOCUMENTS

CN 110809484 A 2/2020
EP 3103492 A1 12/2016
(Continued)

OTHER PUBLICATIONS

International Search Report and Written Opinion in International Appln. No. PCT/EP2022/052801, mailed on Apr. 22, 2022, 10 pages.
(Continued)

*Primary Examiner* — Deanna K Hall

(74) *Attorney, Agent, or Firm* — Fish & Richardson P.C.

(57) ABSTRACT

A dose counting system of an injection device or of a module configured to be used with or applied to an injection device is described. The dose counting system includes a sensor arrangement including a first sensor configured to output a first signal and a second sensor configured to output a second signal; and a processor configured to: detect a peak in the first signal when the first signal has increased by at least a predefined up threshold and the first signal exceeds the value of the second signal by more than a predetermined crossover threshold; determine that a unit of medicament has been administered when the first signal drops from the peak by more than a predefined down threshold and the preceding peak occurred in the second signal; and determine a medi- (Continued)

cament dosage administered by the injection device by counting the administered units of medicament.

20 Claims, 10 Drawing Sheets

(56)                    References Cited

U.S. PATENT DOCUMENTS

2017/0296746  A1    10/2017   Chen et al.
2020/0384205  A1    12/2020   Toporek et al.

FOREIGN PATENT DOCUMENTS

JP            H03-150415  A        6/1991
JP            H06-058770  A        3/1994
JP             2014-520584  A       8/2014
WO      WO 2004/078239           9/2004
WO      WO 2013/004844  A1       1/2013
WO      WO 2014/033195           3/2014
WO      WO 2019/002534  A1       1/2019
WO      WO 2019/101962           5/2019
WO      WO 2019/121452  A1       6/2019
WO      WO 2019/224626          11/2019
WO      WO 2020/110124           6/2020
WO      WO 2022/171548           8/2022

OTHER PUBLICATIONS

International Preliminary Report on Patentability in International Appln. No. PCT/EP2022/052801, mailed on Aug. 24, 2023, 8 pages.

DOSE COUNTING SYSTEM

CROSS REFERENCE TO RELATED APPLICATIONS

The present application is the national stage entry of International Patent Application No. PCT/EP2022/052801, filed on Feb. 7, 2022, and claims priority to Application No. EP 21315018.8, filed on Feb. 9, 2021, the disclosures of which are incorporated herein by reference.

TECHNICAL FIELD

The present disclosure relates to a dose counting system of an injection device or of a module configured to be used with or applied to an injection device and a method of operating the dose counting system.

BACKGROUND

A variety of diseases exists that require regular treatment by injection of a medicament. Such injection can be performed by using injection devices, which are applied either by medical personnel or by patients themselves. As an example, type1 and type2 diabetes can be treated by patients themselves by injection of insulin doses, for example once or several times per day. For instance, a prefilled disposable insulin pen can be used as an injection device. Alternatively, a reusable pen may be used. A reusable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose. WO2019/101962A1 describes an injection device comprising a movable dosage programming component comprising a rotary encoder system having a predefined angular periodicity, a sensor arrangement comprising a first optical sensor configured to detect movement of the movable dosage programming component relative to the sensor arrangement during dosing of a medicament and a second optical sensor configured to detect movement of the rotary encoder system relative to the second optical sensor. The first optical sensor is configured to operate in a strobe-sampling mode at a first frequency and the second optical sensor is configured to operate in a strobe-sampling mode at a second frequency lower than the first frequency. The injection device also comprises a processor arrangement configured to, based on said detected movement, determine a medicament dosage administered by the injection device. WO2019/101962A1 further describes a method for processing signals generated by the sensor arrangement with two optical sensors arranged with a 180° shift such that the signal of the first sensor of the two sensors and the signal of the second sensor of the two sensors are in anti-phase. The method comprises the steps of setting a high threshold and a low threshold for the signal of the first sensor and for the signal of the second sensor, respectively, and counting a unit of a dose selected with the movable dosage programming component if the signal of the second sensor passes the high threshold and thereafter passes the low threshold, and thereafter the signal of the first sensor passes the low threshold and thereafter passes the high threshold.

SUMMARY

A first aspect described herein relates to a dose counting system of an injection device or of a module configured to be used with or applied to an injection device. The dose counting system includes:
  a sensor arrangement comprising a first sensor configured to output a first signal and a second sensor configured to output a second signal, wherein the first sensor and the second sensor have an angular offset relative to each other and wherein the sensor arrangement is configured to detect movement of a rotary encoder system relative to the respective sensor arrangement during dosing of a medicament; and
  a processor configured to:
    detect a peak in the first signal when the first signal has increased by at least a predefined up threshold above the previous minimum of the first signal and the first signal exceeds the value of the second signal by more than a predetermined crossover threshold;
    subsequent to detecting a peak in the first signal, determine that a unit of medicament has been administered when the first signal drops from the peak by more than a predefined down threshold and the preceding peak occurred in the second signal; and
    determine a medicament dosage administered by the injection device by counting the administered units of medicament.

The up threshold and the down threshold may have the same value.

When no previous peak of the first signal exists, the processor may be further configured to: detect an earliest peak in the first signal by modifying the crossover threshold by a factor less than one and/or removing the up threshold criteria and/or by modifying the down threshold by a factor less than one.

The processor may be further configured to: (a) detect a final peak in the first signal by: determining that no subsequent peak has occurred in the second signal; in response, modifying the up threshold by a factor less than one and/or modifying the crossover threshold by a factor less than one; and applying the modified up threshold and/or modified crossover threshold to the first signal to detect the final peak; and (b) determine that the detected final peak in the first signal represents administration of a unit of medicament by removing the down threshold.

The rotary encoder system may comprise an encoder ring comprising a plurality of substantially light reflective flags arranged circumferentially around the encoder ring in accordance with the predefined angular periodicity. The rotary encoder system may be configured to rotate by 15 degrees for each unit of medicament administered and wherein the plurality of substantially light reflective flags are spaced apart by 30 degrees. The angular offset between the first sensor and the second sensor may be 45 degrees, such that the first signal and the second signal are in antiphase.

The dose counting system may further comprise an injection button and an electrical switch connected to the sensor arrangement, the electrical switch arranged to supply power to the sensor arrangement in response to actuation of the injection button. The electrical switch may be arranged to remove the supply of power to the sensor arrangement in response to de-actuation of the injection button and wherein the processor may be configured to determine that a medicament dosage administration is complete when a predetermined time period has elapsed after removal of the power supply to the sensor arrangement.

The dose counting system may further comprise a movable dosage programming component comprising the rotary encoder system and wherein the rotary encoder system has a predefined angular periodicity.

The rotary encoder system may be configured to be rotatable with respect to the first optical sensor during a dialing mode of operation of the injection device and to determine a measured dose dialed into the injection device.

A second aspect disclosed herein relates to a method of operating a dose counting system of an injection device or of a module configured to be used with or applied to an injection device. The dose counting system includes:

a sensor arrangement comprising a first sensor configured to output a first signal and a second sensor configured to output a second signal, wherein the first sensor and the second sensor have an angular offset relative to each other and wherein the sensor arrangement is configured to detect movement of a rotary encoder system relative to the respective sensor arrangement during dosing of a medicament; and a processor;

wherein the method comprises:

detecting a peak in the first signal when the first signal has increased by at least a predefined up threshold above the previous minimum of the first signal and the first signal exceeds the value of the second signal by more than a predetermined crossover threshold;

subsequent to detecting a peak in the first signal, determining that a unit of medicament has been administered when the first signal drops from the peak by more than a predefined down threshold and the preceding peak occurred in the second signal; and determining a medicament dosage administered by the injection device by counting the administered units of medicament.

When no previous peak of the first signal exists, the method of the second aspect further comprises: detecting an earliest peak in the first signal by modifying the crossover threshold by a factor less than one and/or removing the up threshold criteria and/or by modifying the down threshold by a factor less than one.

The method of the second aspect further comprises:

detecting a final peak in the first signal by:

determining that no subsequent peak has occurred in the second signal;

in response, modifying the up threshold by a factor less than one and/or modifying the crossover threshold by a factor less than one; and applying the modified up threshold and/or modified crossover threshold to the first signal to detect the final peak; and determining that the detected final peak in the first signal represents administration of a unit of medicament by removing the down threshold.

BRIEF DESCRIPTION OF THE FIGURES

So that the general concepts set out in the foregoing sections can be more fully understood, embodiments thereof will be described with reference to the accompanying drawings, in which.

DETAILED DESCRIPTION

In the following, embodiments will be described with reference to an insulin injection device. The present disclosure is however not limited to such application and may equally well be deployed with injection devices that eject other medicaments.

Embodiments are provided in relation to injection devices, in particular to variable dose injection devices, which record and/or track data on doses delivered thereby. These data may include the size of the selected dose, the time and date of administration, the duration of the administration and the like. Features described herein include the arrangement of sensing elements, power management techniques (to facilitate small batteries) and a trigger switch arrangement to enable efficient power usage.

Certain embodiments in this document are illustrated with respect to an injection device where an injection button and grip are combined. The mechanical construction of such a device is described in detail in the international patent application WO2014/033195A1, which is incorporated herein by reference. Other injection devices with the same kinematical behaviour of the dial extension and trigger button during dose setting and dose expelling operational mode are known as, for example, the Kwikpen® device marketed by Eli Lilly and the Novopen® device marketed by Novo Nordisk. An application of the general principles to these devices therefore appears straightforward and further explanations will be omitted. However, the general principles of the present disclosure are not limited to that kinematical behaviour. Certain other embodiments may be conceived for application to an injection device where there are separate injection button and grip components like the device described in WO2004078239. The embodiments described in this document may be particularly based on the embodiments described in WO2019/101962A1, which is incorporated herein by reference.

In the following discussion, the terms "distal", "distally" and "distal end" refer to the end of an injection device towards which a needle is provided. The terms "proximal", "proximally" and "proximal end" refer to the opposite end of the injection device towards which an injection button or dosage knob is provided.

Figure 1:
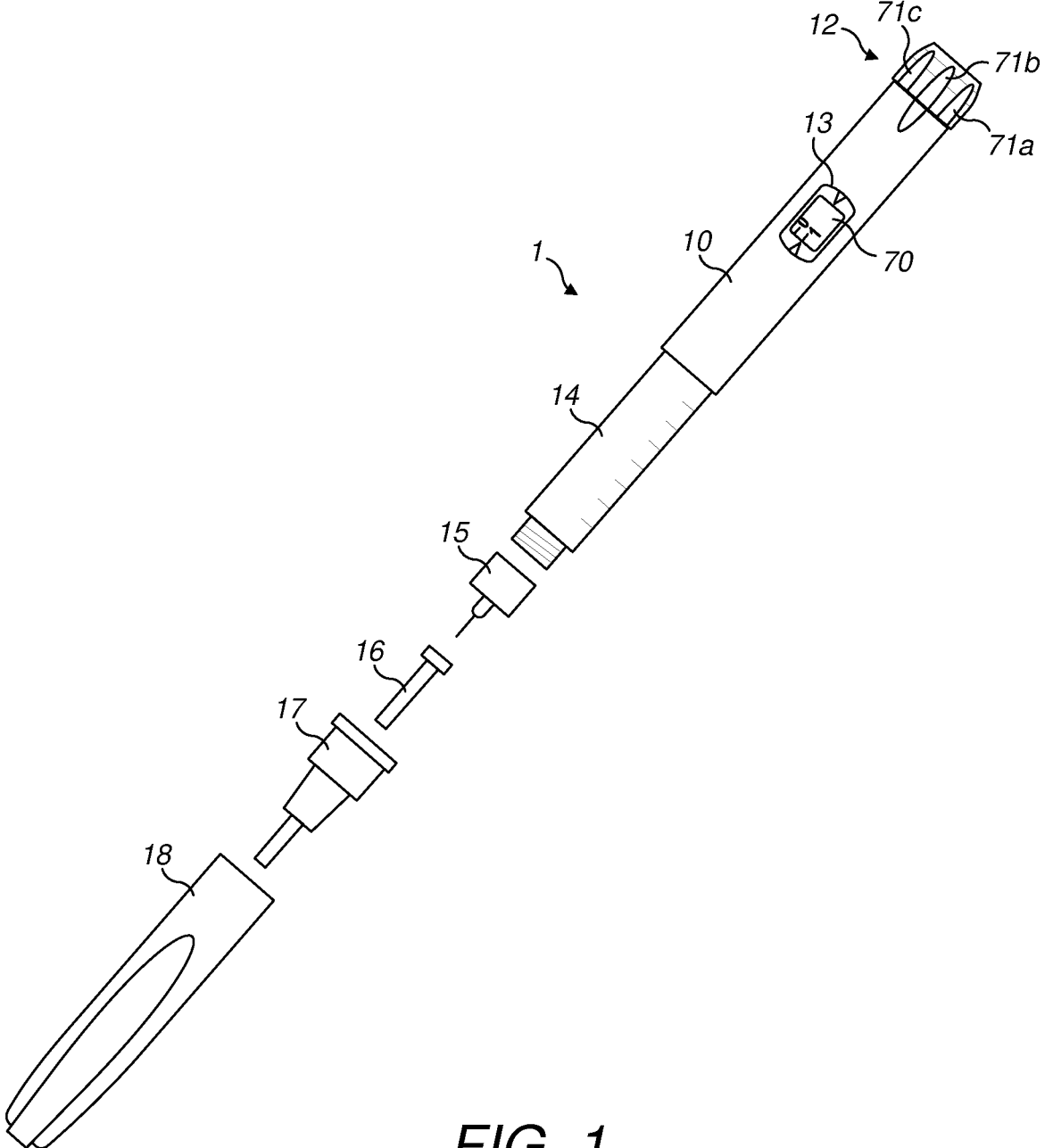
FIG. 1 shows an injection device according to a first embodiment.

FIG. 1 from WO2019/101962A1 is an exploded view of a medicament delivery device. In this example, the medicament delivery device is an injection device 1, such as the injection pen described in WO2014/033195A1.

The injection device 1 of FIG. 1 is a prefilled, disposable injection pen that comprises a housing 10 and contains an insulin container 14, to which a needle 15 can be affixed. The needle is protected by an inner needle cap 16 and either an outer needle cap 17 other cap 18. An insulin dose to be ejected from injection device 1 can be programmed, or 'dialed in' by turning a dosage knob 12, and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve 70 that is configured to move when the dosage knob 12 is turned, to provide a visual indication of a currently programmed dose. The dosage knob 12 is rotated on a helical path with respect to the housing 10 when turned during programming.

In this example, the dosage knob 12 includes one or more formations 71a, 71b, 71c to facilitate attachment of a data collection device.

The injection device 1 may be configured so that turning the dosage knob 12 causes a mechanical click sound to provide acoustical feedback to a user. The dial sleeve 70 mechanically interacts with a piston in insulin container 14. In this embodiment, the dosage knob 12 also acts as an injection button. The dosage knob may house a separate depressible button, or may be an unitary component which the user presses on to effect a dosing process. When needle 15 is stuck into a skin portion of a patient, and then dosage knob 12 is pushed in an axial direction, the insulin dose displayed in display window 13 will be ejected from injection device 1. When the needle 15 of injection device 1 remains for a certain time in the skin portion after the dosage knob 12 is pushed, a high percentage of the dose is actually injected into the patient's body. Ejection of the insulin dose may also cause a mechanical click sound, which is however different from the sounds produced when rotating the dosage knob 12 during dialling of the dose.

In this embodiment, during delivery of the insulin dose, the dosage knob 12 is returned to its initial position in an axial movement, without rotation, while the dial sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing dosage knob 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

As explained above, the dosage knob 12 also functions as an injection button so that the same component is used for dialling and dispensing.

Figure 3A:
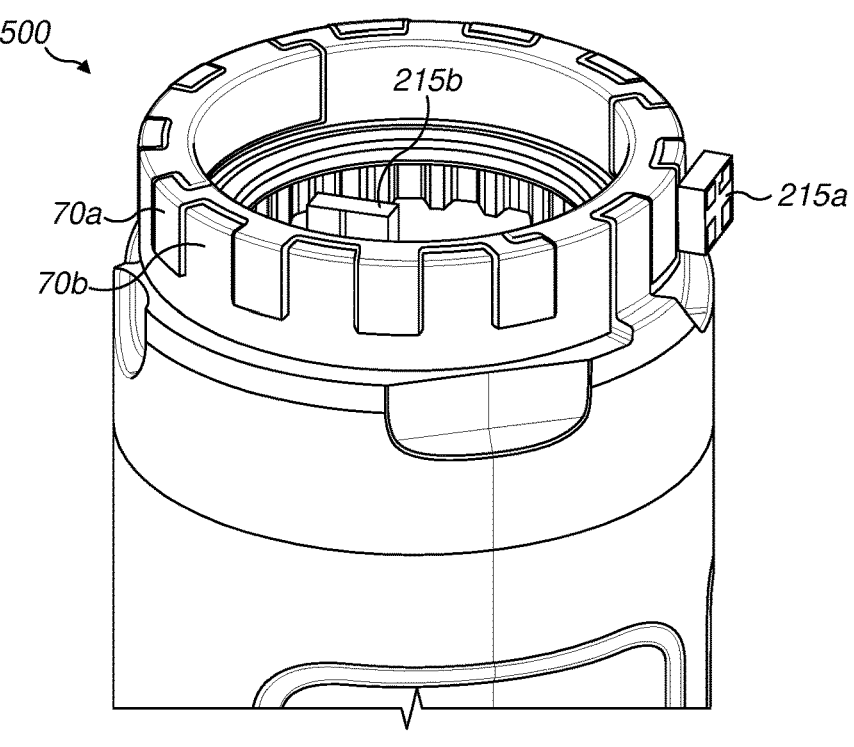
FIG. 3A is an elevated side view of a first type of encoder system.
Figure 3B:
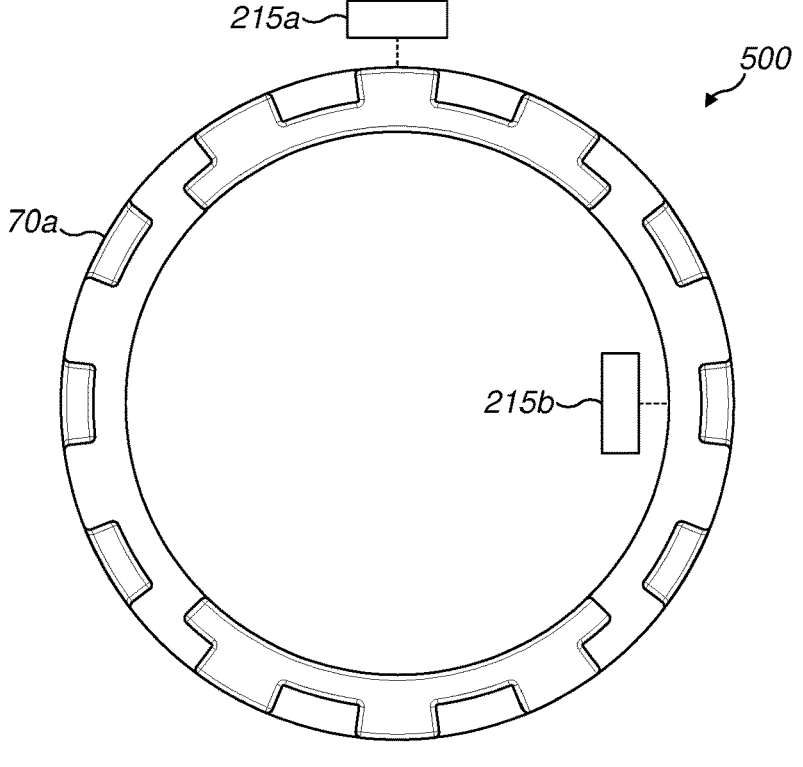
FIG. 3B is a plan view of the encoder system shown in FIG. 3A.

FIGS. 3A and 3B show an encoder system 500 according to certain embodiments. The encoder system may be configured for use with the injection device 1 described above. As shown in FIG. 3A and FIG. 3B, the primary sensor 215a and secondary sensor 215b are configured to target specially adapted regions at the proximal end of the dial sleeve 70. In this embodiment, the primary sensor 215a and secondary sensor 215b are infrared (IR) reflective sensors. Therefore, the specially adapted proximal regions of the dial sleeve 70 are divided into a reflective area 70a and a non-reflective (or absorbent) area 70b. The part of the dial sleeve 70 comprising the reflective area 70a and a non-reflective (or absorbent) area 70b may be termed an encoder ring.

Having two sensors facilitates a power management technique described below. The primary sensor 215a is arranged to target a series of alternating reflective regions 70a and non-reflective regions 70b at a frequency commensurate with the resolution required for the dose history requirements applicable to a particular drug or dosing regime, for example, 1 IU. The secondary sensor 215b is arranged to target a series of alternating reflective regions 70a and non-reflective regions 70b at a reduced frequency compared to the primary sensor 215a. It should be understood that the encoder system 500 could function with only a primary sensor 215a to measure the dispensed dose. The secondary sensor 215b facilitates the power management technique described below.

The two sets of encoded regions 70a, 70b are shown in FIGS. 3A and 3B concentrically with one external and the other internal. However, any suitable arrangement of the two encoded regions 70a, 70b is possible. Whilst the regions 70a, 70b are shown as castellated regions, it should be borne in mind that other shapes and configurations are possible.

Figure 2:
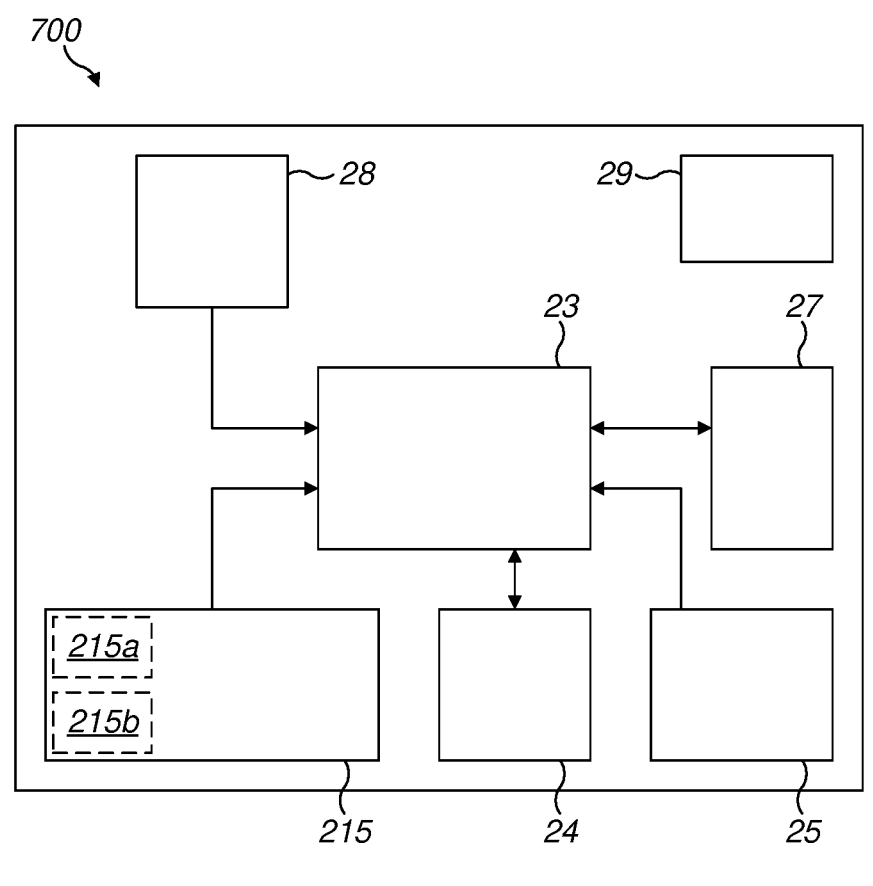
FIG. 2 is a schematic block diagram of a dose counting system.

A dose counting system 700 is shown schematically in FIG. 2. The dose counting system 700 may be an integral part of the injection device 1 or part of a module configured to be attached to the injection device 1. The dose counting system 700 comprises a processor arrangement 23 including one or more processors, such as a microprocessor, a Digital Signal Processor (DSP), Application Specific Integrated Circuit (ASIC), Field Programmable Gate Array (FPGA) or the like, together with memory units 24, 25, including program memory 24 and main memory 25, which can store software for execution by the processor arrangement 23.

The dose counting system 700 controls a sensor arrangement 215, comprising one or more sensors 215a, 215b.

An output 27 is provided, which may be a wireless communications interface for communicating with another device via a wireless network such as Wi-Fi or Bluetooth®, or an interface for a wired communications link, such as a socket for receiving a Universal Series Bus (USB), mini-USB or micro-USB connector. For example, data may be output to a data collection device attached to the device 1.

A power switch 28 is also provided, together with a battery 29.

Power Management

It is advantageous to be able to minimise the power usage of the dose counting system 700 so that the size of a battery 29 needed to be packaged into the device 1 can be minimised. The sensors 215a, 215b used in this embodiment require a certain amount of power to operate. This embodiment is arranged such that the sensors 215a, 215b can be switched on and off intermittently at a controlled frequency (i.e. in a strobe-sampling mode). There is inherently a limit to the maximum rotational speed that can be counted by a sampled encoder system before aliasing occurs. Aliasing is the phenomenon where the sampling rate is less than the rate at which sensed regions pass the sensor which means that a miscount could occur when a region change is missed. The secondary sensor 215b with a reduced frequency compared to the primary frequency 215a can tolerate a higher rotational speed before it too becomes aliased. Whilst the secondary sensor 215b is not able to resolve the dose dispensed to the same resolution as the primary sensor 215a, the output of the secondary sensor 215b remains reliable at higher speeds. Therefore both sensors 215a, 215b are used in combination to be able to accurately determine dose delivered up to a first threshold rotational (dispensing) speed. The sensors 215a, 215b can then be used to determine an approximate dose delivered up to a second (higher) threshold dosing speed. At speeds above the second threshold speed the sensors 215a, 215b will not be able to accurately or approximately determine the dose delivered, therefore the second threshold is set above a speed which is not physically possible in the injection device 12.

The first speed threshold is determined by the sampling rate of primary sensor 215a and the frequency of encoder region transitions, which is fixed at the resolution required by the intended drug or dosing regime (for example one transition per 1 IU). The second speed threshold is determined by the sampling rate of the secondary sensor 215b and the frequency of encoder region transitions. The first threshold is set such that the largest range of dispensing speeds can be covered by the system for accurate reporting of dose dispensed.

The example embodiment shown in FIG. 3B has primary sensor 215a targeting region transitions at 1 transition per 1 IU of dose delivered and the secondary sensor 215b targeting region transitions at 1 transition per 6 IU of dose delivered. Other options are possible which include 1 transition per 2 IU, 1 transition per 4 IU, 1 transition per 8 IU and 1 transition per 12 IU units. These options are each possible because there are 24 separate regions 70a, 70b per revolution in the encoder system 500 shown in FIG. 3B. In general, if the number of separate regions 70a, 70b per revolution were n units then there would be options at one region transition per m units where m was any integer factor of n greater than 1 and less than n.

The slower the sampling frequency of both sensors 215a, 215b, the lower the power consumption required and therefore the smaller the required size of the battery 29. It is therefore optimal to minimise, by design, the sampling frequency as far as is practical.

The following embodiments relate to an alternative sensing technique to determine the number of medicament units that have been dispensed from the device 1.

As with the embodiments described above, two sensors 215 are mounted in the injection button 12 and are configured to sense the relative rotational position of the dial sleeve 70 relative to the injection button during the dispensing of a dose. This relative rotation can be equated to the size of the dose dispensed and used for the purpose of generating and storing or displaying dose history information.

Figure 4A:
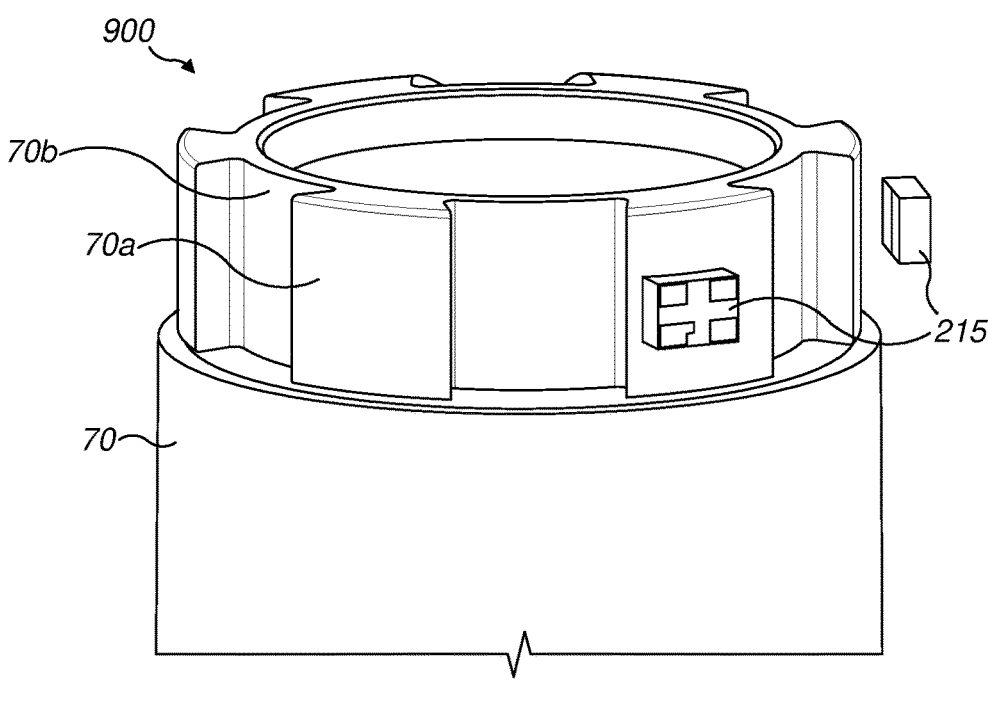
FIG. 4A is an elevated side view of a second type of encoder system.

As shown in FIG. 4A, the two sensors 215 from this embodiment are configured to target specially adapted regions 70a, 70b of the dial sleeve 70. In this embodiment IR reflective sensors are used, therefore the regions of the dial sleeve 70 are divided into reflective and absorbent segments 70a, 70b. The segments 70a, 70b may also be referred to herein as flags.

Figure 4B:
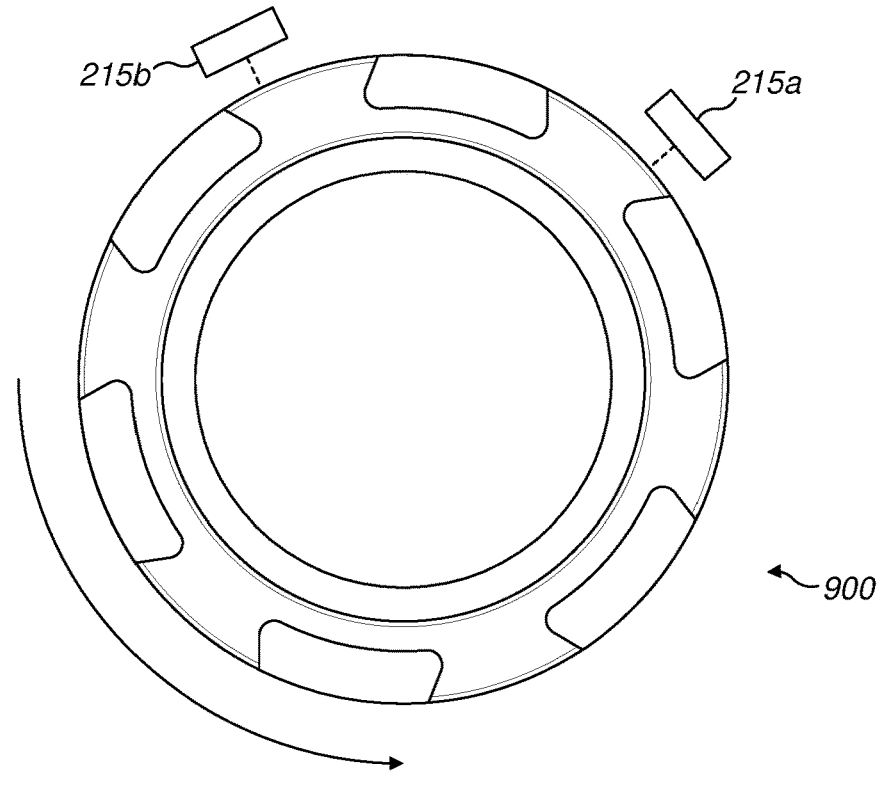
FIG. 4B is a plan view of the encoder system shown in FIG. 4A.

Unlike the encoder system 500 described above in relation to FIGS. 3A and 3B, the encoder system 900 shown in FIGS. 4A and 4B has both IR sensors 215 target the same type of region 70a, 70b. In other words, the sensors 215 are arranged so that they both face reflective regions 70a or both face absorbent regions 70b at the same time. During the dispensing of a dose, the dial sleeve 70 rotates anti-clockwise 15° relative to the injection button 12 for every medicament unit that has been dispensed. The alternate flag elements are in 30° (or two unit) sections. The sensors 215 are arranged to be out of phase with each other, such that the angle between them equates to an odd number of units (e.g. 15°, 45°, 75°, etc.), as shown in FIG. 4B.

The encoder system 900 shown in FIG. 4B has 12 units per revolution, i.e. 12 alternating regions 70a, 70b. In general, embodiments work with any multiple of 4 units per revolution. The angle, α, between sensors 215 can be expressed by Equation 1, where both m and n are any integers and there are 4m units dispensed per revolution.

$$\alpha = (2n - 1)\frac{360}{4m}$$

Equation 1 – Angle between sensors

Figure 10:
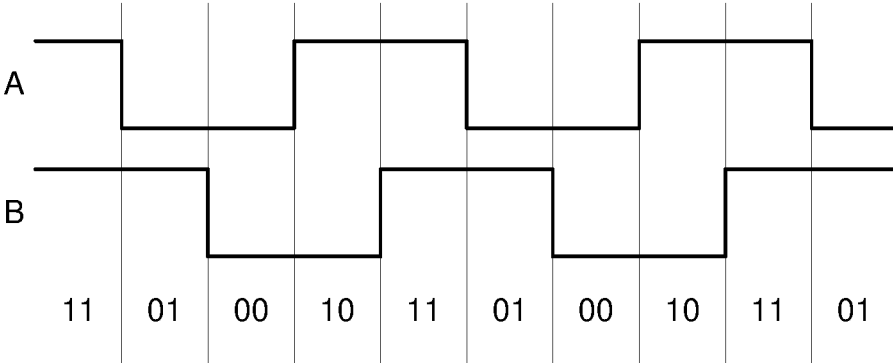
FIG. 10 illustrates a Gray code output with an optical dose counting system having an alternative arrangement.
Figure 10:
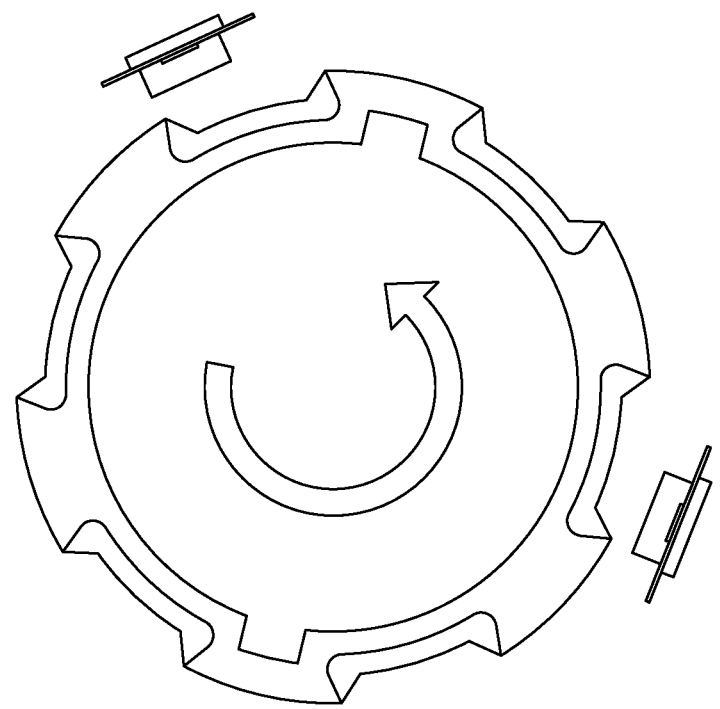

FIG. 10 shows how the outputs for a Sensor A and Sensor B change as the dial sleeve 70 rotates anti-clockwise during dispensing of a medicament.

In combination, the two sensors A, B produce a 2-bit Gray code output (11, 01, 00, 10). The 2-bit code sequence repeats every four units dispensed. This coded output facilitates the detection of positive (anticlockwise) and negative (clockwise) rotations. For example, when the sensors read '11' a change to '01' would be a positive rotation and the change to '10' would be a negative rotation. This directionally sensitive system has advantages over a purely incremental system, in the ability to accurately determine true dispensed dose volume in the cases where negative rotations can occur. For example, in mechanisms that over rotate at the end of dose stop before 'backing-off' when the user releases the injection button 12.

Figure 5A:
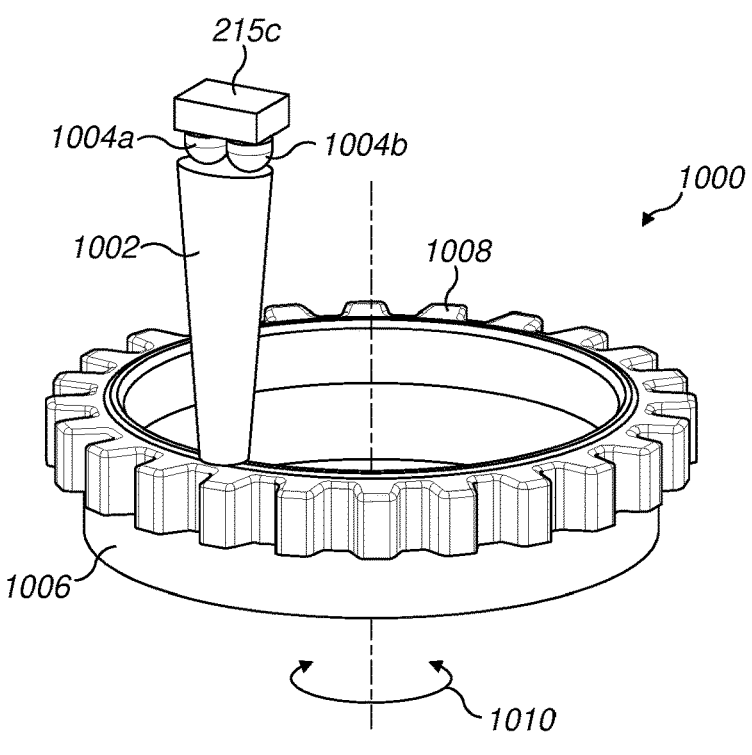
FIG. 5A is an elevated side view of an eight type of encoder system.
Figure 5B:
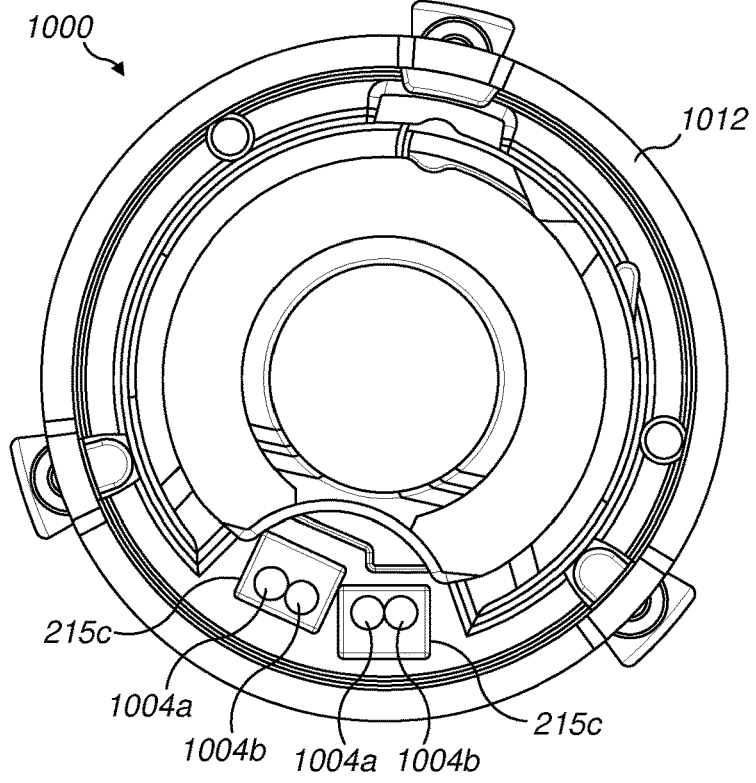
FIG. 5B is a plan view of the encoder system shown in FIG. 5A.

An encoder system according to further embodiments will now be described with reference to FIGS. 5A and 5B. This encoder system may be used to record doses that are delivered from the injection device. The concept of this encoder system is based on a light guide used to convey the status of an indicator flag to a reflective sensor, which is located physically remote to the flag. The embodiments shown in FIGS. 5A and 5B use an optical add-on module configured to be attached to an injection device. For simplicity, the housing of the add-on module is omitted and only the sensor and optical components are shown in FIGS. 5A and 5B. The add-on module also contains a dose counting system 700, such as that shown in FIG. 2. Such an add-on module may be configured to be added to a suitably configured pen injection device for the purpose of recording doses that are dialled and delivered from the device. The add-on module may be configured to replace the dialling knob/injection button of an injection pen, or alternatively may fit over the existing dialling knob/injection button. In these embodiments, the indicator flag is formed by a relative rotation of a number sleeve or the dial sleeve and the add-on module, the latter of which houses at least one optical sensor. This functionality may be of value to a wide variety of device users as a memory aid or to support detailed logging of dose history. The add-on module may be configured to be connectable to an external device such as a smartphone or a tablet PC, or similar, to enable the dose history to be downloaded from the module on a periodic basis. However, the concept of the encoder system is also applicable to any device with the indicator flag and sensor separation, for example the injection device 1 of FIG. 1, wherein the module may be implemented in the dosage knob 12, which could be removable.

According to the encoder system concept, a collimating optics is arranged between the active face of at least one optical sensor, which may be a IR reflective sensor, and a movable dosage programming component. The collimating optics may comprise one or more discrete collimating lenses and one or more light pipes. The lens geometry may be selected to parallelize ("collimate") divergent radiation emitted by the at least one optical sensor prior to transmission through the light pipe between the at least one sensor and the target, namely the indicator flag.

FIG. 5A shows essential parts of an embodiment of a module 1000 implementing this encoder concept: an indicator flag 1008 may be formed by relative rotation of a number sleeve 1006 around a rotation axis 1010, wherein the indicator flag 1008 is implemented in the shown embodiment by radially projecting teeth, formed in the top of for example the number sleeve or the dial sleeve 70 of the injection device 1; an optical sensor 215c and collimating optics comprising two collimating lenses 1004a, 1004b and a light guidance in the form of a light pipe 1002 for conveying the status of the indicator flag 1008 to the sensor 215c which is located remote from the flag. The collimating optics 1002, 1004a, 1004b and the optical sensor 215c may be positioned relative to surrounding components within the injection device and particularly associated to an add-on module. As can be seen, the collimating optics comprising the lenses 1004a, 1004 and the light pipe 1002 are arranged between the active side, i.e. the IR emitting and receiving side of the optical sensor 215c and the indicator flag 1008 formed by the number sleeve 1006.

FIG. 5B shows a chassis 1012 housing two optical sensors 215c (represented by their locations in the chassis 1012 shown by the rectangles with bold lines) and their respective collimating lenses 1004a, 1004b according to an embodiment of a module 1000. The collimating lenses 1004a, 1004b, here implemented by discrete lenses, are envisaged to be held relative to the optical sensors 215c and proximal face of the light pipes by means of a cradle or other locating geometry existing as a feature within the chassis 1012.

All of the above points relate, fundamentally, to more robust encoding mechanical system where an optical (reflective) sensor form the active element in an optical encoder. If the motion of the number sleeve relative to the dose button is more efficiently captured, reduced emitter power of an optical sensor and the use of algorithms requiring fewer microcontroller operations can be utilized, reducing energy consumption and extending battery life. The encoder system described herein is equally applicable to inclusion in a disposable or a re-usable injection device, or any device containing an optical encoder arrangement with a similar light pipe architecture.

Figure 6:
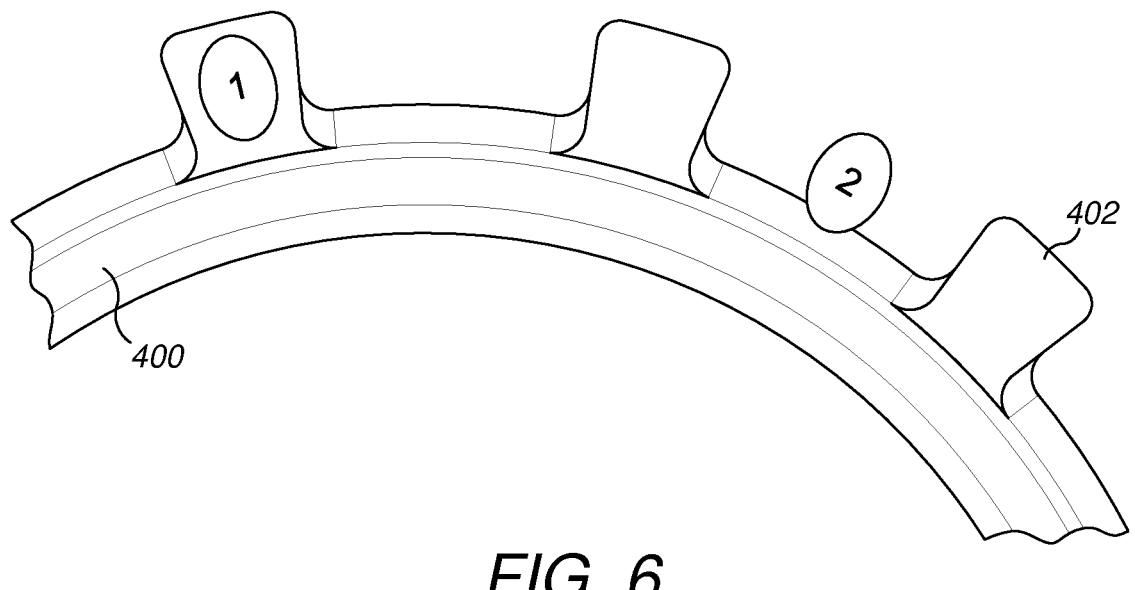
FIG. 6 is a detailed view on an encoder system.

FIG. 6 shows a partial view of a number sleeve 400 and the arrangement of teeth or flags 402 on the number sleeve. The flags 402 are substantially light reflecting. For example, the flags 402 may be made of or coated with a reflective material, or the reflective material may be printed on the surface of the flags 402. The flags 402 are spaced by an angle of 30 degrees form each other, such that there are twelve flags 402 evenly spaced around the circumference of the number sleeve 400. FIG. 6 also shows exemplary positions of two light pipes associated with respective optical sensors, indicated by the ovals numbered 1 and 2. The light pipes are separated by an angle of degrees, such that the difference between the angular separation go the light pipes and the angular separation of the flags 402 is 15 degrees and the signals from the two sensors are out of phase with each other. In some embodiments of an injection device, the number sleeve 400 is configured to rotate by 15 degrees for each unit of medicament dialled or delivered. The arrangement shown in FIG. 6 therefore allows the signals from the two sensors to be used to measure the numbered of dialled or delivered units of medicament. Although this embodiment has been described in terms of optical sensing and reflective flags, in some other embodiments inductive, capacitive or magnetic sensing may be used. For example, the flags 402 may comprise conductive or magnetic regions which pass under inductive, capacitive or magnetic sensors in order to determine the amount of rotation of the number sleeve 400.

Next, embodiments of an algorithm for processing the signals, particularly signal voltages, generated by the optical sensors of sensor arrangements as described above with regard to the injection device and the module are described. The algorithm is implemented as a computer program for execution by one or more processors, for example of the processor arrangement 23 comprised by the dose counting system 700 as shown in FIG. 2.

The algorithm is implemented for processing the signals delivered by the one or more optical sensors 215a, 215b, 215c, namely for decoding the selected medicament dosage for delivery by or delivered by an injection device. The algorithm is preferably applicable to devices with an indicator flag and sensor separation with light pipes such as the module as described above.

The relative rotation between the dose button and the number sleeve may be encoded optically using an incremental encoder, for example a quadrature encoder, with two or more optical sensors, particularly reflective IR sensors, looking axially at castellations or radially projecting teeth or flags, formed on the top surface of the number sleeve. The encoder system may be implemented as an addon module, which means that the position of the castellations or teeth being detected may vary relative to the positions of the optical sensors from device to device, even after calibration of the module due to the variation of the manufacturing process of the injection device to which the module is fitted. It is therefore likely that there will be variation in signal between devices and during typical usage. Additionally, while the dose button is being depressed and released, the axial position of the optical sensors may also vary relative to the castellations.

The algorithm described in the following may be implemented in an injection device or an addon module particularly for the purpose of recording doses that are delivered from the injection device. This functionality may be of value to a wide variety of injection device users as a memory aid or to support detailed logging of dose history. It is envisaged that the electronics implementing the algorithms may be configured to be connectable to a mobile device such as a smartphone, or similar, to enable the dose history to be downloaded from the electronics on a periodic basis.

The algorithm is configured for detecting the relative rotation of castellations or teeth on a number sleeve relative to a nonrotating component such as the dose button. The presence or otherwise of a castellation or tooth feature provides a binary code, which may be used to count the number of units dispensed from the injection device. The voltage output of the optical sensors may be typically approximated to a sinusoid. The algorithm is able to detect the presence or otherwise of a castellation or tooth feature across all devices, which may have any combination of geometrical tolerances on the physical features.

Additionally, as the dose button moves axially towards or away from the castellation or tooth features at the beginning and end of dose ejection, the change in the signal generated by the optical sensor should not be incorrectly interpreted as a rotation of the castellation or tooth features. Therefore, the algorithm may accommodate significant amplitude modulation of the signal generated by the optical sensor.

Figure 7:
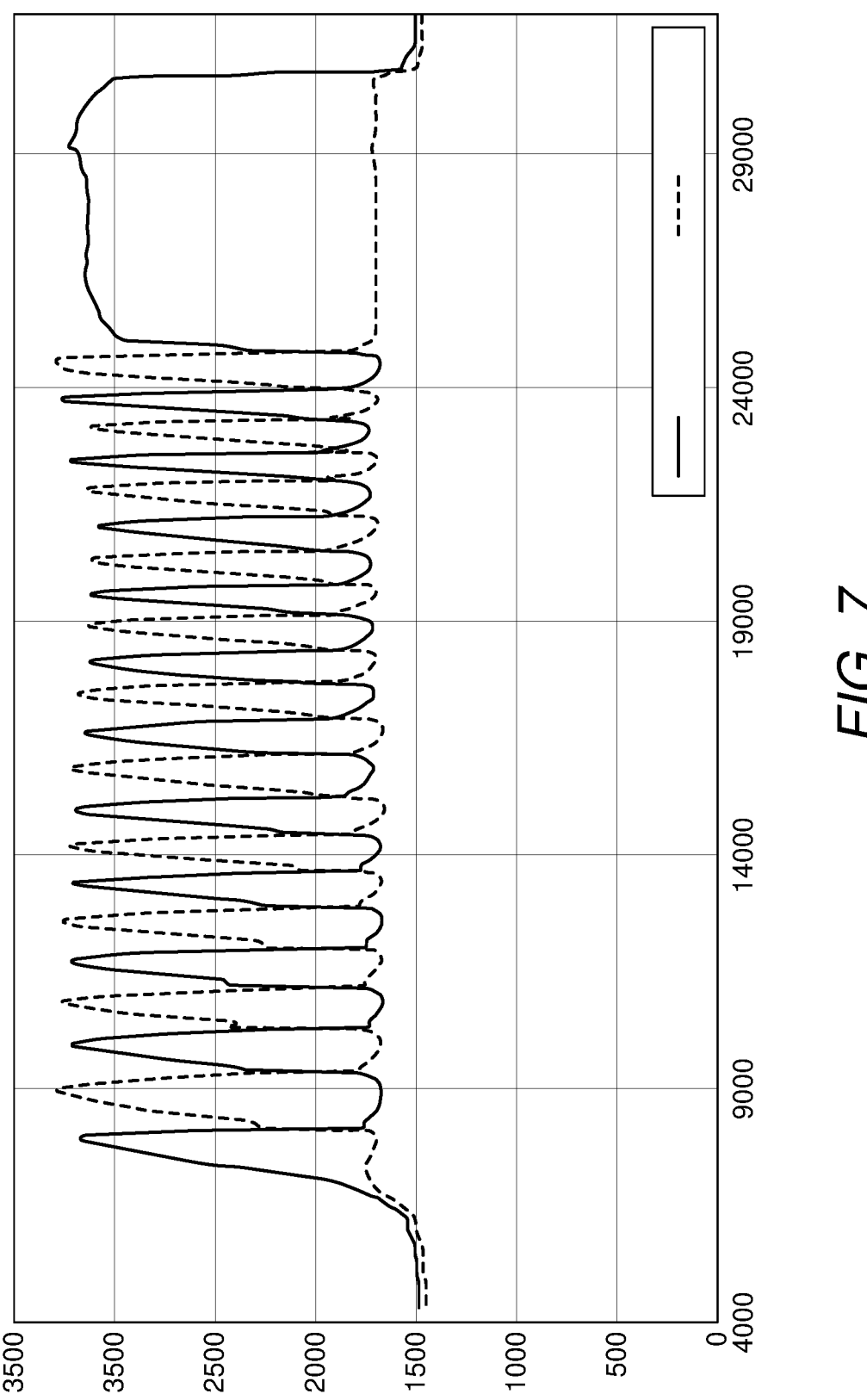
FIG. 7 shows the course of signal voltages generated by two optical sensors of a sensor arrangement during movement of a movable dosage programming component relative to the sensor arrangement when a dosage is dispensed with an injection device.

FIG. 7 shows the typical course of the signal voltages generated by two optical sensors, which may have a different gain profile to each other, during a typical medicament dispense operation. The output of the first sensor is illustrated by a solid line, while the output of the second sensor is illustrated by a dashed line. The x axis shows the sample number, while the y axis shows the sensor signal amplitude. The signal voltages are amplitude modulated. The different gain profiles may lead to significantly different signal voltages being generated by the two optical sensors and sent to a processor for processing the signal voltages. The different gain profiles may be for example due to tolerances associated with electronic components.

The algorithm pertains to a system with two optical sensors being arranged with a 180° phase shift so that the signal voltages generated by both sensors are antiphase.

Figure 8:
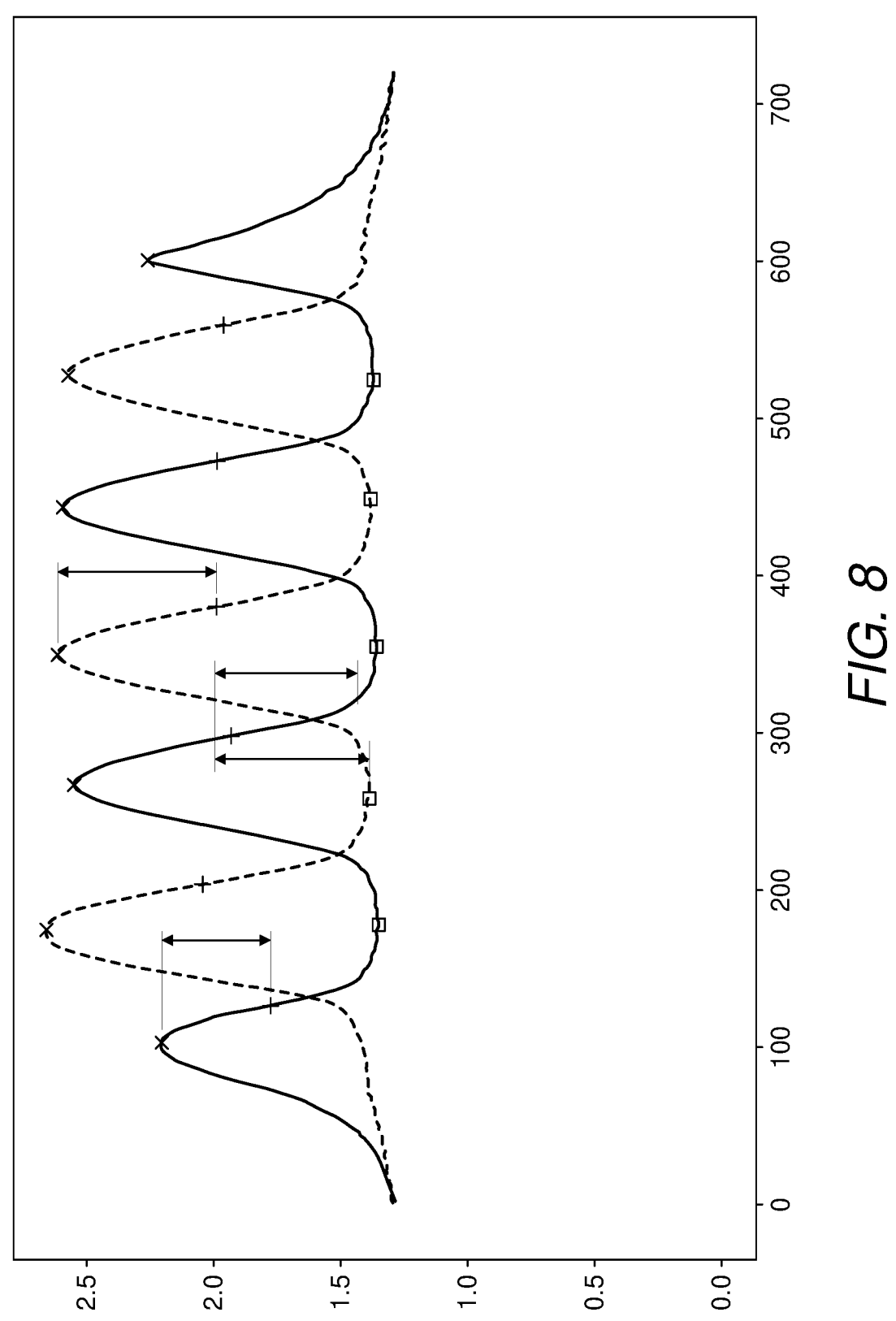
FIG. 8 shows threshold definitions for a dosage determining algorithm.
Figure 9:
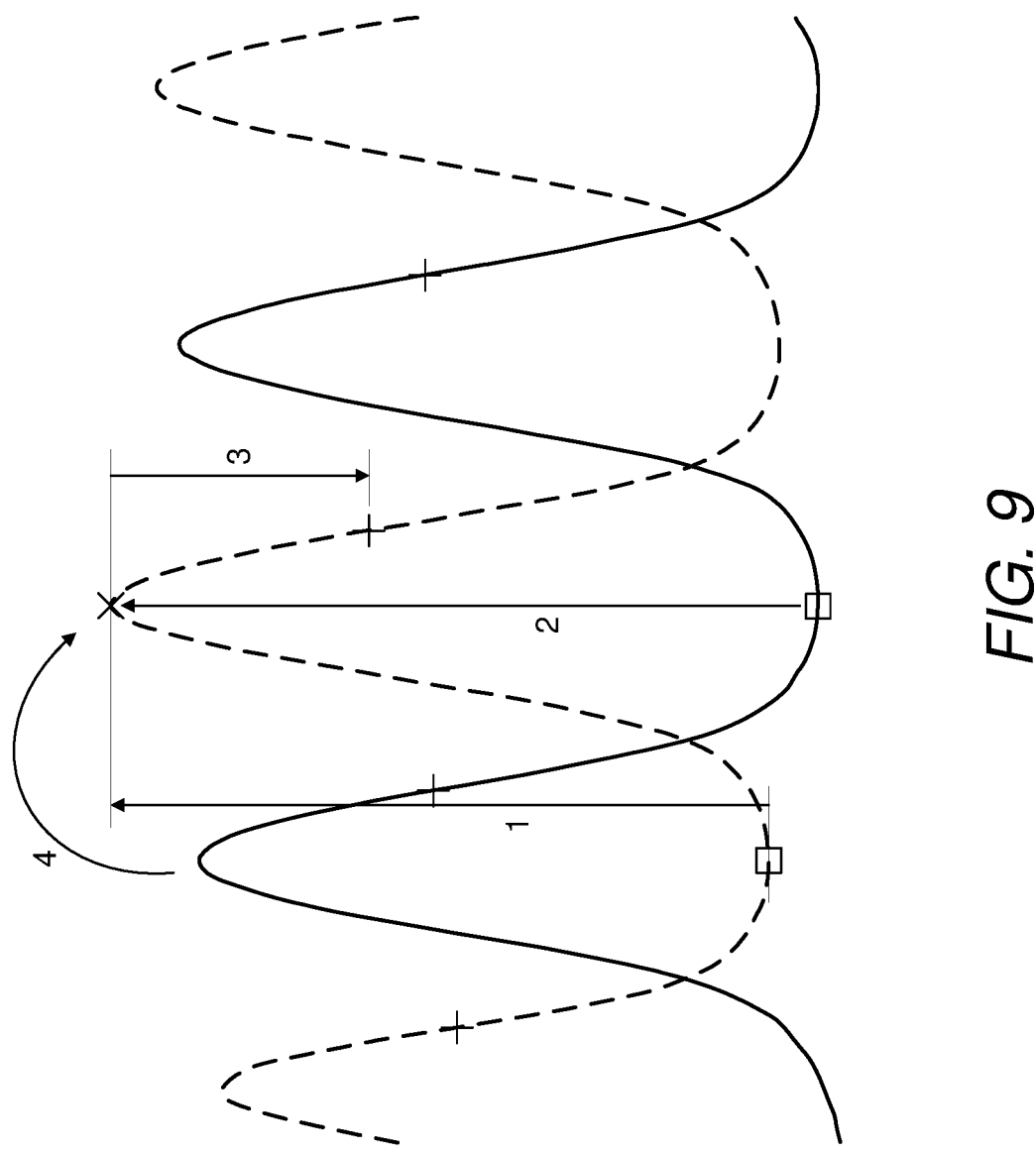
FIG. 9 shows the conditions for dose detection for the dosage determining algorithm.

An embodiment of the algorithm applies several criteria, first to detect a peak in the signals from the two optical sensors and then to determine that the peak should be counted as a unit of medicament that has been delivered from the injection device. These criteria are also illustrated in FIGS. 8 and 9. This algorithm is based on two sensors observing rotation of castellations or flags on a number sleeve and outputting first and second signals respectively which are out of phase with each other. FIG. 8 shows the typical course of the signal voltages generated by two optical sensors, during a typical medicament dispense operation. The output of the first sensor is illustrated by a solid line, while the output of the second sensor is illustrated by a dashed line. The x axis shows the sample number, while the y axis shows the sensor signal amplitude.

Firstly, the algorithm defines an "up" threshold, which is an amount by which a signal must increase above the previous minimum of that signal. Once a signal increases above the up threshold, it becomes valid to detect a peak in that signal. The algorithm also defines a "crossover" threshold. For the algorithm to detect a peak in the first signal, the first signal must also exceed the value of the second signal by more than the crossover threshold. Once these two conditions are met, the next maximum of the first signal is detected as a peak. The crosses shown on the signal traces in FIG. 8 show where the algorithm has identified a peak in the respective signal. The squares shown on the signal traces in FIG. 8 show where the algorithm has identified a minimum point in the respective signal.

Subsequent to detecting a peak in the first signal, the algorithm determines whether the peak should be counted as a unit of medicament delivered. The algorithm defines a "down" threshold, which is an amount by which a signal must decrease below the peak of that signal. Once a signal decreases from the detected peak below the down threshold, it becomes valid to determine that the peak represents a unit of medicament delivered. For the algorithm to determine that the peak in the first signal represents a unit of medicament delivered, it must be determined that the previous peak occurred in the second signal. In other words, the algorithm must determine that the peaks occur alternately in the first and second signals in order to count them as units of medicament delivered. The plus signs shown on the signal traces in FIG. 8 illustrate the point at which the algorithm has determined that the previous peak should be counted as a unit of medicament delivered.

These four criteria are illustrated in FIG. 9, in which arrow "1" shows the up threshold being exceeded, arrow "2" shows the crossover threshold being exceeded, arrow "3" shows the down threshold being exceeded and arrow "4" shows that the algorithm has determined that the previous peak was in the other of the two signals. Again the crosses in FIG. 9 show where the algorithm has identified a peak in the respective signal; the squares in FIG. 9 show where the algorithm has identified a minimum point in the respective signal and the plus signs in FIG. 9 illustrate the point at which the algorithm has determined that the previous peak should be counted as a unit of medicament delivered.

In some embodiments of the algorithm the up threshold and the down threshold may have the same value. The up threshold and the down threshold may in fact be defined in the algorithm as a single "updown" threshold. The up threshold, down threshold and crossover threshold may be set separately for each module, based on measurements of the sensor amplitudes for that module. This makes the system less sensitive to some of the variation in optical performance due to, for example, batch-to-batch variation of optical sensor performance.

There is very little time dependence in the algorithm described above. This ensures that the speed of operation of the injection device has little effect on the accuracy and reliability of the dose counting. The algorithm can therefore cope with a large range of injection speeds without suffering any loss in performance.

Using the crossover threshold, which sets a minimum value on the difference between the two channels, makes the system more robust to unusual user behaviour. It means that a larger rotation of the Number Sleeve is required (>7.5°) in order to detect a peak in a signal and ultimately to count a dose, which helps in some of the use situations described below.

The algorithm is designed to be robust to unusual user behaviour, ensuring that the module counts doses accurately in all situations without counting falsely when no drug has been dispensed from the injection device. Some examples of behaviour that cause unusual changes in the sensor signals are listed below—the method described mitigates the risk of dose count errors in these situations, amongst others:

(a) The user pushes the button of the injection device inwards without having dialled a dose and applies some torque to the button before releasing it. This causes some motion of the number sleeve and castellations/flags in the injection device relative to the module, and hence a change in the sensor signals which must not be recorded as dispensed unit by the module.

(b) The user dials and then dispenses only part of the dialled dose, they then pause and release pressure from the injection device, before continuing to complete the dose. This additional action mid-dose causes additional motion of the mechanism components that is not present in a typical dose, and hence additional changes in the optical signals. Depending on the exact point at which the dose is paused, and the user technique, the changes to the optical signal can appear similar to an additional unit of drug being dispensed, or one less unit of drug being dispensed. It is important that the module is able to recognise the actual delivered dose in these cases without errors.

(c) Very fast injections can cause additional movement of mechanism components beyond a typical dispense speed. The changes to the optical signal as a result of this can appear similar to additional units of drug being dispensed.

A dose switch, alternatively termed a wake-up switch, is triggered ON by axial movement of the button. The dose switch controls when the two sensors are turned on, and thus when the first dose counting algorithm begins to run.

The algorithm may also feature additional functionality for detecting the first and last peak occurring in the signals from the two sensors.

In some embodiments and use situations, the first peak can occur due to axial movement of the number sleeve only. As the dose button is pushed in to initiate dispense, the sensors move axially closer to the flags and one sensor is initially positioned over a flag and therefore starts with a high signal value. If no dose is dialled in, then pressing the dose button may still result in a peak in the sensor readings. It is therefore important to detect the first peak, but not to count it as a dosed unit. Part of the criteria for detecting all subsequent peaks is that the signal has increased above the previous minimum of that signal. However, where a maximum in a signal is detected, but there is no previous peak in that signal, the algorithm performs a first peak analysis. In this analysis, one or more of the thresholds are reduced or removed to allow for the fact that the first peak will likely be smaller than the subsequent peaks. The algorithm defines a "First Peak" factor which is less than one. The crossover threshold may be modified by the first peak factor, meaning that the first signal does not to be as large relative to the second signal to be detected as a peak. Furthermore the up threshold may be removed entirely, since there may be no previous minimum to measure the peak against. The algorithm may also modify the down threshold by the first peak factor or by a different factor less than one. Since the first peak is smaller than the subsequent peaks, it also needs to drop by less to be detected. The algorithm may employ one or more of the above modifications to detect the first peak.

The different treatment for the first peak allows for the fact that the first peak can be smaller than the following peaks. This is due to the fact that the dose button is still moving axially inwards as the Number Sleeve starts to rotate, so the axial gap to the sensors is larger and the signal weaker.

The algorithm also applies some special criteria for detecting the final peak. If a maximum is detected in the first signal and it is also determined that no subsequent maximum has occurred in the second signal, then the maximum in the first signal is treated as the final peak, and a final peak analysis is performed. In this analysis, one or more of the thresholds are reduced or removed to allow for the fact that the final peak will likely be smaller than the previous peaks. The algorithm defines a "Last Peak" factor which is less than one. The up threshold and/or the crossover threshold are modified by the last peak factor, or by two different last peak factors which are each less than one. This means that the first signal does not to increase by as much relative to its last minimum and/or be as large relative to the second signal to be detected as a peak. Furthermore the down threshold may be removed entirely, since the amount by which the first signal decreases after the last peak may be small. The same process would apply if the final peak occurs in the second signal.

The different treatment of the last peak mitigates the risk of dose count errors in situations where the signal stays high in one channel at the end of a dose, for example:

If the axial tolerances of the dose switch mean that it turns off while the button is still pushed in quite far.

If the user keeps the dose button pushed in for a long time at the end of dose and the sensors time out.

The algorithm has been described above in relation to detection of the delivered dose. However, in some embodiments the two sensors may be powered on in advance of a dose dialling and used to detect and measure the dose dialling. The algorithm may be used for this purpose, or a different algorithm may be applied when detecting the dialled dose. Alternatively a completely separate sensor arrangement may be provided for measuring the dialled dose. In addition the injection device may be provided with an end of dose switch, which is activated only when the dialled dose (or dose remaining to be dispensed) reaches zero.

The algorithm is arranged to terminate according to the following criteria:

(a) After a normal dose this, 100 ms after the dose switch is disconnected (goes low); or (b) After a timeout when the injection button is pressed (dose switch activated) and the measured dose is zero for a predetermined period of time, for example 20 seconds; or (c) After a timeout when the injection button is pressed (dose switch activated) and the measured dose is not equal to zero and there is no dialled dose count increase for a predetermined period of time, for example 5 seconds.

Each module or injection device may be calibrated during manufacture. This may be used to set the maximum and minimum expected values for the signals. During manufacture, a set of calibration geometry may be passed beneath each sensor at controlled distances to record the largest and smallest signal voltage. The calibration process may also set the values for the up threshold, down threshold and crossover threshold. The calibration process may also set the 'emit' pulse width of each sensor (i.e. the proportion of time per sample that the emitter LED is on for). The emit pulse widths can be set, for example, to match the mean amplitude of the two sensors, or to maximise the peak-to-trough of the sensor.

While the embodiments above have been described in relation to collecting data from an insulin injector pen, it is noted that embodiments of the invention may be used for other purposes, such as monitoring of injections of other medicaments.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®), B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

17

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A dose counting system of an injection device or of a module configured to be used with or applied to an injection device, the dose counting system comprising:
   a sensor arrangement comprising a first sensor configured to output a first signal and a second sensor configured to output a second signal, wherein the first sensor and the second sensor have an angular offset relative to each other and wherein the sensor arrangement is configured to detect movement of a rotary encoder system relative to the sensor arrangement during dosing of a medicament; and
   a processor configured to:
      detect a peak in the first signal when the first signal has increased by at least a predefined up threshold above the previous minimum of the first signal and the first signal exceeds the value of the second signal by more than a predetermined crossover threshold;
      subsequent to detecting a peak in the first signal, determine that a unit of medicament has been administered when the first signal drops from the peak by more than a predefined down threshold and a preceding peak occurred in the second signal; and
      determine a medicament dosage administered by the injection device by counting the administered units of medicament.

2. The dose counting system according to claim 1, wherein the up threshold and the down threshold have the same value.

3. The dose counting system according to claim 1, wherein when no previous peak of the first signal exists, the processor is further configured to:
   detect an earliest peak in the first signal by modifying the crossover threshold by a factor less than one and/or removing the up threshold criteria and/or
   by modifying the down threshold by a factor less than one.

4. The dose counting system according to claim 1, wherein the processor is further configured to:
   detect a final peak in the first signal by:
      determining that no subsequent peak has occurred in the second signal;
      in response, modifying the up threshold by a factor less than one and/or modifying the crossover threshold by a factor less than one; and
      applying the modified up threshold and/or modified crossover threshold to the first signal to detect the final peak; and determine that the detected final peak in the first signal represents administration of a unit of medicament by removing the down threshold.

5. The dose counting system according to claim 1, wherein the rotary encoder system comprises an encoder ring comprising a plurality of substantially light reflective flags arranged circumferentially around the encoder ring in accordance with a predefined angular periodicity.

6. The dose counting system according to claim 5, wherein the rotary encoder system is configured to rotate by 15 degrees for each unit of medicament administered and wherein the plurality of substantially light reflective flags are spaced apart by 30 degrees.

7. The dose counting system according to claim 6, wherein the angular offset between the first sensor and the second sensor is 45 degrees, such that the first signal and the second signal are in antiphase.

8. The dose counting system according to claim 1, further comprising an injection button and an electrical switch connected to the sensor arrangement, the electrical switch arranged to supply power to the sensor arrangement in response to actuation of the injection button.

9. The dose counting system according to claim 8, wherein the electrical switch is arranged to remove a supply of power to the sensor arrangement in response to de-actuation of the injection button and wherein the processor is configured to determine that a medicament dosage administration is complete when a predetermined time period has elapsed after removal of the supply of power to the sensor arrangement.

10. The dose counting system according to claim 1, further comprising a movable dosage programming component comprising the rotary encoder system and wherein the rotary encoder system has a predefined angular periodicity.

11. The dose counting system according to claim 1, wherein the rotary encoder system is configured to be rotatable with respect to the first sensor during a dialling mode of operation of the injection device and to determine a measured dose dialled into the injection device.

12. A method of operating a dose counting system of an injection device or of a module configured to be used with or applied to an injection device, the dose counting system comprising:

a sensor arrangement comprising a first sensor configured to output a first signal and a second sensor configured to output a second signal, wherein the first sensor and the second sensor have an angular offset relative to each other and wherein the sensor arrangement is configured to detect movement of a rotary encoder system relative to the sensor arrangement during dosing of a medicament; and a processor;

wherein the method comprises:

detecting a peak in the first signal when the first signal has increased by at least a predefined up threshold above the previous minimum of the first signal and the first signal exceeds the value of the second signal by more than a predetermined crossover threshold;

subsequent to detecting a peak in the first signal, determining that a unit of medicament has been administered when the first signal drops from the peak by more than a predefined down threshold and the preceding peak occurred in the second signal; and determining a medicament dosage administered by the injection device by counting the administered units of medicament.

13. The method according to claim 12, wherein the up threshold and the down threshold have the same value.

14. The method according to claim 12, wherein when no previous peak of the first signal exists, the method further comprises:

detecting an earliest peak in the first signal by modifying the crossover threshold by a factor less than one and/or removing the up threshold criteria and/or by modifying the down threshold by a factor less than one.

15. The method according to claim 12, wherein the method further comprises:

detecting a final peak in the first signal by:

determining that no subsequent peak has occurred in the second signal;

in response, modifying the up threshold by a factor less than one and/or modifying the crossover threshold by a factor less than one; and applying the modified up threshold and/or modified crossover threshold to the first signal to detect the final peak; and determining that the detected final peak in the first signal represents administration of a unit of medicament by removing the down threshold.

16. The method according to claim 12, wherein the rotary encoder system comprises an encoder ring comprising a plurality of substantially light reflective flags arranged circumferentially around the encoder ring in accordance with the predefined angular periodicity.

17. The method according to claim 16, wherein the rotary encoder system is configured to rotate by 15 degrees for each unit of medicament administered and wherein the plurality of substantially light reflective flags are spaced apart by 30 degrees.

18. The method according to claim 17, wherein the angular offset between the first sensor and the second sensor is 45 degrees, such that the first signal and the second signal are in antiphase.

19. The method according to claim 12, wherein the dose counting system further comprises: an injection button and an electrical switch connected to the sensor arrangement, wherein the electrical switch is arranged to supply power to the sensor arrangement in response to actuation of the injection button.

20. The method according to claim 19, wherein the electrical switch is arranged to remove the supply of power to the sensor arrangement in response to de-actuation of the injection button, and wherein the method further comprises determining that a medicament dosage administration is complete when a predetermined time period has elapsed after removal of the power supply to the sensor arrangement.

* * * * *